United States Patent
Sharma et al.

(10) Patent No.: US 11,523,613 B2
(45) Date of Patent: Dec. 13, 2022

(54) FERRATE COMPOSITIONS FOR SURFACE DISINFECTION

(71) Applicants: THE TEXAS A&M UNIVERSITY SYSTEM, College Station, TX (US); The United States Government as Represented by the Department of Veterans Affairs, Washington, DC (US)

(72) Inventors: Virender K. Sharma, College Station, TX (US); Chetan Jinadatha, Belton, TX (US)

(73) Assignees: The Texas A&M University System, College Station, TX (US); The United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/494,001

(22) PCT Filed: Mar. 16, 2018

(86) PCT No.: PCT/US2018/022983
§ 371 (c)(1),
(2) Date: Sep. 13, 2019

(87) PCT Pub. No.: WO2018/170463
PCT Pub. Date: Sep. 20, 2018

(65) Prior Publication Data
US 2020/0085063 A1    Mar. 19, 2020

Related U.S. Application Data (60) Provisional application No. 62/472,356, filed on Mar. 16, 2017.

(51) Int. Cl.
*A01N 59/16* (2006.01)
*A01N 25/02* (2006.01)
*A01N 25/30* (2006.01)
*A01N 59/08* (2006.01)

(52) U.S. Cl.
CPC ............. *A01N 59/16* (2013.01); *A01N 25/02* (2013.01); *A01N 25/30* (2013.01); *A01N 59/08* (2013.01)

(58) Field of Classification Search
CPC ........ A01N 59/16; A01N 25/02; A01N 25/30; A01N 59/08
See application file for complete search history.

(56) References Cited

U.S. PATENT DOCUMENTS

| | | | |
|---|---|---|---|
| 6,267,896 B1 | 7/2001 | Patterson et al. | |
| 2008/0274930 A1* | 11/2008 | Smith | C11D 3/044 510/221 |

(Continued)

OTHER PUBLICATIONS

Hoffman, M., The best non-toxic ways to clean your home, 2008, WebMD from https://www.webmd.com/a-to-z-guides/features/best-nontoxic-ways-to-clean-home (Year: 2008).*

(Continued)

*Primary Examiner* — Bethany P Barham
*Assistant Examiner* — Ayaan A Alam
(74) *Attorney, Agent, or Firm* — Christensen O'Connor Johnson Kindness PLLC (57) ABSTRACT

Methods for disinfecting a surface are provided which include contacting a surface with a solution comprising $Fe(VI)O_4^{2-}$, thereby disinfecting the surfaces. In some cases, the surface to be contacted with the solution is in a space suitable for human occupancy and the surface is arranged in the ambient of the space. In addition, solutions comprising $Fe(VI)O_4^{2-}$ are provided. The solutions may additionally include a hypohalite salt and a surfactant.

10 Claims, 3 Drawing Sheets

(56) References Cited

U.S. PATENT DOCUMENTS

2011/0023913 A1 2/2011 Fulling
2011/0076223 A1 3/2011 Sharma
2011/0268672 A1 11/2011 Monzyk

OTHER PUBLICATIONS

Blades, N., 2020, Distilled water, nourish by WebMD, from https://www.webmd.com/diet/distilled-water-overview# (Year: 2020).*
Maghraoui, A., 2015, Effect of degree of ClO—hypochlorite on the wet synthesis offerrate (VI), Advances in Materials Physics and Chemistry, 5, 133-139 (Year: 2015).*
Ferrate(VI), Wikipedia Article (Jul. 27, 2016) retrieved on May 4, 2018 from https://en.wikipedia.org/w/index.php?title=Ferrate(VI)&oldid=731738741.
Extended European Search Report dated Oct. 21, 2020, in corresponding European Patent Application No. 18767085.6, filed Mar. 16, 2018, 7 pages.
Jiang, J., et al., "Progress in the development and use of ferrate(VI) salt as an oxidant and coagulant for water and wastewater treatment", Water Research, 36:1397-1408, 2002.
Indian Office Action dated Mar. 31, 2021, from Indian Application No. 201937037902, filed Sep. 19, 2019, 7 pages.
Gilbert, M.B., et al., "Analytical Notes—An Investigation of the Applicability of Ferrate Ion for Disinfection", American Waterworks Association, 68(9), doi:10.1002/j. 1551-8833.1976.tb02456.x, 495-497, 1976.

* cited by examiner

FERRATE COMPOSITIONS FOR SURFACE DISINFECTION

CROSS-REFERENCE TO RELATED APPLICATION

The present application claims the benefit of U.S. Application No. 62/472,356, filed Mar. 16, 2017, expressly incorporated herein by reference in its entirety.

STATEMENT OF GOVERNMENT LICENSE RIGHTS

This invention was made with Government support under award number 1637040 awarded by the National Science Foundation. The Government has certain rights in the invention.

BACKGROUND OF THE INVENTION

There has been increasing concern of infections related to visits to hospitals, called hospital-acquired infections (HAIs). HAIs have resulted in significant cases of mortality. Approximately fifty percent of such susceptible-to-death circumstances are related to not properly cleaning or disinfecting at hospitals surfaces, such as hospital beds, hospital room floors, and medical devices. Common disinfectants used for cleaning surfaces include bleach (i.e. sodium hypochlorite), hydrogen peroxide, and salt containing central positively charged nitrogen atom surrounded by four organic groups (or quaternary salts). These disinfectants can clean the surfaces effectively, but in performing their disinfection functions often destroy or damage hospital equipment and materials. In addition, these disinfectants often have off-putting odor and can cause irritation of the eyes and skin of end users. Further, in the health care environment, pathogens associated with surfaces frequently resist disinfection and, therefore, microbial surface contamination may persist even after routine cleaning.

In recent years, tetraoxy iron in +6 oxidation state ($Fe^{VI}O_4^{2-}$), commonly called "ferrate", has been shown to be a potential disinfectant for treating water and wastewater. It is a potential disinfectant due to its ability to inactivate a wide variety of microorganisms (*Escherichia coli, Staphylococcus aureus, Shigella flexneri,* and *Salmonella typhimurium*) at a low dosage in water.

In addition, ferrate reduces to Fe(III), forming no harmful byproducts, and is, therefore, a potentially environmentally friendly disinfectant compared to the unpleasant and harmful by-products formed from conventional disinfectants, such as chlorine fumes from 10% sodium hypochlorite. Moreover, ferrate is potentially superior disinfectant to other commonly used disinfectants, such as quaternary ammonium compounds, because of its ability to inactivate sulfite-reducing clostridia spores, which cannot be inactivated by quaternary ammonium compounds. Added advantages include the ability to use ferrate as an oxidant/coagulant to treat wastewater of hospitals contaminated with unused pharmaceuticals.

Substantial research has been done on ferrate in a bulk-solution, aqueous environments. However, no study has been carried out on ferrate as a potential surface disinfectant. Because the mechanism of surface disinfection can be completely different on surfaces than in solution it has been unclear whether ferrate solutions can disinfect surfaces.

Despite advances in bulk-solution disinfection, a need exists for improved surface disinfection, particularly in health care settings. The present invention seeks to fulfill this need and provides further related advantages.

SUMMARY OF THE INVENTION

In one aspect, the present application provides methods for disinfecting a surface, which addresses the problems associated with currently used surface disinfectants. In certain embodiments, the method comprises contacting the surface with a solution comprising $Fe(VI)O_4^{2-}$, thereby disinfecting the surface. In some cases, the surface to be contacted with such a solution is in a space suitable for human occupancy and the surface is arranged in the ambient of the space.

In another aspect, the disclosed herein are solutions comprising $Fe(VI)O_4^{2-}$. In some embodiments, the solutions additionally include a hypohalite salt, such as calcium hypochlorite or sodium hypochlorite. In additional or alternative embodiments, the solutions include a surfactant.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

As shown herein, a solution comprising ferrate is an effective surface disinfectant. Accordingly, in one aspect, the present application provides method of disinfecting a surface comprising: contacting the surface with a solution comprising $Fe^{VI}O_4^{2-}$, thereby disinfecting the surface. As used herein, $Fe^{VI}O_4^{2-}$, also referred to interchangeably as "ferrate", "$Fe(VI)O_4^{2-}$", and "ferrate(VI)", refers to tetraoxy iron in +6 oxidation state with the chemical formula $[FeO_4]^{2-}$. Ferrate may also be referred to herein as an "oxycompound of iron in an oxidation state of six".

As used herein, the term "disinfecting" refers to killing, destroying, or otherwise disabling a microorganism (i.e. rendering microorganisms incapable of reproducing and/or infecting a host organism, such as a person). In certain embodiments, disinfecting includes killing one to 100 million organisms. Microorganisms that may be killed or otherwise rendered incapable of reproducing and/or infecting a host organism include bacteria, viruses, fungi, archaea, protozoa, and algae. Representative microoganisms include *Escherichia coli, Staphylococcus aureus, Shigella flexneri, Salmonella typhimurium, Clostridium difficile* bacteria and spores, Rhinovirus, Norovirus, Zika virus, Ebola virus,

*Aspergillus*, amoeba, helminthic eggs, and *Histoplasma*. The disinfectants and methods described herein may be used to disinfect antibiotic-resistant microorganisms as well, such as but not limited to methicillin-resistant *Staphylococcus aureus* (MRSA).

In certain embodiments, disinfecting a surface using the disinfectant solutions and methods disclosed herein reduces the iron in $Fe(VI)O_4^{2-}$ from Fe(VI) to Fe(III) or Fe(II). In certain embodiments, the by-products of disinfecting reactions between ferrate and microorganisms are non-toxic or otherwise harmless byproducts, such as Fe(III).

As noted above, the present application provides methods for disinfecting a surface, particularly contacting a surface with a solution comprising $Fe(VI)O_4^{2-}$, thereby disinfecting the surface. Surfaces that can be disinfected by the disinfectants and methods disclosed include any surface having the potential to have microorganisms thereon. Example materials having surfaces which may be disinfected by the methods disclosed herein include but are not limited to glass, ceramic, metal, wall paper, painted walls, laminate, solid surfaces such as Corian, granite, quartz and plastic. In some embodiments, a surface to be disinfected may be porous, such as, for example, a woven material. In other cases, the surface to be disinfected may not be porous. In any case, the surface to be disinfected may, in some embodiments, be in a space suitable for human occupancy and the surface may be arranged in the ambient of the space. The phrase "a space which is suitable for human occupancy", as used herein, refers to a space in which an adult human being of average size may comfortably occupy for at least a period of time to eat, sleep, work, lounge, partake in an activity, or complete a task therein. In some cases, spaces suitable for human occupancy may be bounded and include a door for entering and exiting the room. In other cases, a space suitable for human occupancy may be an area with indeterminate boundaries. Examples of spaces which are suitable for human occupancy include but are not limited to single patient rooms, multiple occupancy patient rooms, bathrooms, walk-in closets, hallways, bedrooms, offices, operating rooms, patient examination rooms, waiting and/or lounging areas and nursing stations.

Examples of environments or establishments which may have spaces suitable for human occupancy and which may be considered for the methods disclosed herein include but are not limited to residential buildings, educational facilities, hospitality establishments (such as but not limited to hotels, restaurants, spas, amusement parks and cruise ships), vehicles, workplace facilities, businesses (such as but not limited to gyms, movie theatres and stores), parks, bathrooms, and the like. In certain embodiments, the surfaces are in healthcare facilities, such as but not limited to hospitals, nursing homes, hospices, out-patient facilities, dentists' offices, pharmacies, and the like. Specific areas of interest in a healthcare facility for the disinfectants and methods disclosed herein include patient care areas and operating rooms. Although the methods and disinfectants disclosed herein may additionally or alternatively be used to disinfect medical devices and equipment, the methods and disinfectants may be used to disinfect surfaces of non-medical items in a healthcare environment. Examples of surfaces that may be considered for disinfection in a health care facility include but are not limited to hospital beds, a hospital floor, non-sterilizable medical equipment, and tray tables.

Although the methods and disinfectants disclosed herein may be used in laboratory spaces, particularly since such areas are suitable for human occupancy, in some cases use of the methods and disinfectants disclosed herein may be specific to non-laboratory spaces. In particular, the methods and disinfectants disclosed herein may be specific to disinfecting and, sometimes, cleaning (through the use of one or more surfactants in the disinfectant solution as described in more detail below) spaces which are not associated with chemical testing and production or have regulations about not having food in the space. More specifically, the methods disclosed herein are distinguishable from processes performed in a laboratory for producing, testing and/or analyzing ferrate solutions.

The idea of the methods disclosed herein being specifically used on surfaces in spaces suitable for human occupancy may sometimes correspond to using the methods and ferrate disinfection solutions disclosed herein to perform area/room disinfection processes. As used herein, "area/room disinfection processes" refer to disinfection processes performed in an area or room that is suitable for human occupancy to deactivate, destroy or prevent the growth of disease-carrying microorganisms in the area/room. The processes may involve disinfecting any surfaces in an area/room, including objects that are fixed in the area/room, objects that are moveable in the area/room and/or surfaces defining the confines of the area/room, such as the floor, ceiling, walls, windows and/or doors. In many cases, area/room disinfection processes concentrate on surfaces in a region between approximately 2 feet and approximately 4 feet from a floor of an area or room. Such a region is considered a "high touch" region of a room or area since objects of frequent use are generally placed in such a region. Examples of objects typically found in a high touch zone of an area or room include but are not limited to desktops, keyboards, telephones, chairs, door and cabinet handles, light switches and sinks. Examples of objects in high touch zones of hospital rooms additionally or alternatively include beds, bedside tables, tray tables and intravenous stands. Due to such a region being considered a high touch zone, it is generally considered the area of highest probability to come in contact with germs and some studies indicate that the high touch zone may be the area having the highest concentration of germs. In some cases, the methods disclosed herein may be specific to contacting surfaces in a high touch region of a room or area (i.e., a region between approximately 2 feet and approximately 4 feet from a floor of an area or room).

An aspect often associated with area/room disinfection processes that may be included in the methods disclosed herein is that the disinfection process may be conducted in accordance with a schedule. In particular, the methods disclosed herein may include scheduling a disinfection or cleaning event for the space and then the process of contacting the one or more surfaces with the ferrate disinfectant solution may be performed at a time specified for the disinfection or cleaning event. Furthermore, the methods disclosed herein may be specific to contacting surfaces of objects arranged in an ambient of a space, particularly objects arranged with respect to one or more activities performed by one or more previous occupants of the space. In particular, the methods disclosed herein may involve contacting surfaces within a room or area with a ferrate disinfectant solution without rearranging items in the room or area specifically for disinfection purposes prior thereto. In yet other embodiments, items may be specifically arranged prior to contacting them with the ferrate disinfectant solution in an effort to increase the efficiency of the disinfection process.

In some cases, the methods disclosed herein may include storing the disinfectant solution in a container prior to the step of contacting the one or more surfaces with the disinfectant solution. In some further embodiments, the method may include mixing one or more materials within the container to produce the disinfectant solution. Such a process may be done in the space in which the disinfection process may be performed or may be done in a separate location. In any case, the container may, in some embodiments, include one or more color indicators signifying predetermined disinfectant strengths for comparison of the ferrate disinfectant solution produced and/or stored in the container. In particular, ferrate solutions typically exhibit a purple hue having a color value (i.e., the relative degree of lightness or darkness) which generally correlates to the disinfection strength of the ferrate solution (i.e., its ability to disinfect microorganisms in a prescribed amount of time). In general, the darker the purple hue a ferrate solution has, the high disinfection efficacy the solution will exhibit. As such, in some cases, the container may include one or more purple indicators signifying predetermined disinfectant strengths for comparison of the ferrate disinfectant solution stored in the container. In some cases, a particular color indicator on the container may signify the threshold at which the disinfectant solution should or should not be used for a disinfection process (i.e., when a disinfectant solution has a comparable or darker hue than the particular color indicator, the disinfectant solution may be used as a disinfectant or when the disinfection solution has a lighter hue than the particular color indicator, the disinfectant solution should not be used as a disinfectant).

In general, the process of contacting surface/s with a ferrate solution may include any known technique for dispersing a fluid on to a surface. Examples of applications include but are not limited to spraying, misting, wiping, and pouring the disinfectant solution on a surface, including any combination thereof. With some applications, the disinfectant solution may be simply applied without the need for its subsequent removal from the surface. In particular, in some cases, the disinfectant solution may evaporate without leaving any residue on the surface. In other cases, the methods disclosed herein may include removing the disinfectant solution from the surface/s. It is contemplated that some materials may need to have the disinfectant solution removed from its surface. Due to the rapid effect of the disinfectant solution, the removal step may be performed any time after a lapse of at least 30 seconds, 15 seconds, or 5 seconds after the one or more surfaces are contacted with the ferrate solution.

In some embodiments, the methods described herein further include neutralizing and discarding any ferrate solution not used during the disinfection process. Alternatively, if the remaining solution has sufficient disinfection strength, it may be stored for a subsequent disinfection process (for surface disinfection or otherwise). As discussed in more detail below, the stability of ferrate solutions vary depending on their composition. In general, the stability of a ferrate solution (i.e., the length of time a ferrate solution is considered to have sufficient disinfection strength to disinfect a surface) may vary from a few hours to a couple of weeks, depending on the composition of the solution. In view of this, the methods disclosed herein may, in some embodiments, include forming a ferrate solution and then within a relatively short time thereafter (such as within an hour) apply the solution to one or more surfaces for disinfection thereof. In other cases, a ferrate solution may be formed and not applied to a surface for several hours or days. In yet other embodiments, a ferrate solution may be formed, stored for a few hours or days, and then applied to a surface and possibly stored again thereafter. In any case, any acid may be added to the ferrate solution to neutralize the solution (i.e., to decompose the ferrate to Fe(II) or Fe(III)) such that it may be disposed of in compliance with environmental guidelines.

Set forth in detail below are ferrate disinfection solutions which may be used for the methods disclosed herein. It is noted, however, that the methods disclosed herein are not necessarily so limited. In particular, it is contemplated that any ferrate solution with a sufficient amount of disinfection strength may be suitable for the methods disclosed herein.

As set forth below, disinfectant solutions are provided which include $Fe(VI)O_4^{2-}$ and a solvent. In some embodiments, the disinfectant solution further includes a hypohalite salt, such as calcium hypochlorite or sodium hypochlorite. In additional or alternative embodiments, the solution includes a surfactant. In any case, in some embodiments, the material comprising $Fe(VI)O_4^{2-}$ in the disinfectant solutions disclosed herein further includes an alkali metal or an alkaline earth metal. Although the disinfection solutions described below have been found to be particularly suitable for disinfecting surfaces, it is noted that the disinfectant solutions are not so limited. In particular, the disinfectant solutions may be used for any application, disinfection or otherwise, in which a ferrate solution may be desirable.

In some embodiments, the disinfectant solutions considered herein have a concentration of $Fe(VI)O_4^{2-}$ between about 1 μM and about 1000 μM in the solution. In certain embodiments, the concentration of $Fe(VI)O_4^{2-}$ in a disinfectant solution is between about 10 μM and about 700 μM and, and in particular cases, the concentration of $Fe(VI)O_4^{2-}$ in a disinfectant solution is between about 100 μM and about 400 μM. Without wishing to be bound by theory, the disinfectant solutions having a concentration of $Fe(VI)O_4^{2-}$ greater than about 400 μM may be less functional in some instances (i.e., have a lower disinfection efficacy) than disinfection solutions having a concentration of $Fe(VI)O_4^{2-}$ less than about 400 μM due to higher pH values exhibited in disinfection solutions having a concentration of $Fe(VI)O_4^{2-}$ greater than about 400 μM. Thus, in certain embodiments, the concentration of $Fe(VI)O_4^{2-}$ desirable for disinfecting bacteria on surfaces is between about 10 μM and about 400 μM, and in other embodiments, the concentration of $Fe(VI)O_4^{2-}$ desirable for disinfecting spores on surfaces may be between about 100 μM and about 400 μM.

In certain embodiments, the ferrate disinfectant solutions disclosed herein include a hypohalite salt, such as sodium hypochlorite or calcium hypochlorite. Sodium hypochlorite has been found to aid in the stability of a ferrate solution, particularly reducing the rate of decay of ferrate in a solution. In some embodiments, ferrate solutions comprising a hypohalite salt are referred to as stabilized ferrate solutions. FIG. 1 illustrates such findings, particularly showing the decay of solutions including $Fe(VI)O_4^{2-}$ at concentrations of 50 μM, 100 μM, 200 μM, and 400 μM with sodium hypochlorite (e.g., household "bleach") concentrations of 0%, 0.02%, 0.05%, 0.1%, 0.5% and 1.0% as a function of time. It is further contemplated that a sodium hypochlorite is useful in helping to further disinfect surfaces in synergy with ferrate. In other embodiments, it may be advantageous to use calcium hypochlorite in a ferrate disinfection solution. In particular, calcium hypochlorite exists in a solid form (typically as powder) at room temperature and thus can offer more convenient means for facilitating the production of a ferrate solution, particularly if it is made at the site (e.g., within the building) that it is going to be decontaminated. More specifically, the amount of solid calcium hypochlorite needed to form a ferrate concentration having a particular concentration of the hypochlorite will generally be less than the amount of liquid sodium hypochlorite needed to do the same. As such, the storage, transport and handling of calcium hypochlorite within a facility is generally easier than the storage, transport and handling of sodium hypochlorite. In any case, the disinfectant solutions disclosed herein can, in some embodiments, include a concentration of a hypohalite salt between about 0.001 wt % and about 1.0 wt %, between about 0.05 wt % and about 1.0 wt %, or between about 0.1 wt % and about 0.5 wt %. In certain embodiments, the concentration of a hypohalite salt in the disinfectant solutions disclosed herein is between about 0.05 wt % and about 0.2 wt %.

Regardless of whether a disinfectant solution includes a hypohalite salt, the disinfectant solutions disclosed herein can, in some embodiments, include one or more surfactants. In some cases, surfactants having cleaning properties (referred to herein as "detergent surfactants") can be used to provide cleaning functionality to the disinfectant solutions disclosed herein, allowing surfaces to be cleaned and disinfected at the same time. The term "cleaning", as used herein, refers to the removal of foreign matter from a surface, such as but not limited to dirt, dust, or other organic materials. The detergent surfactants which can be included in the disinfectant solutions disclosed herein may be anionic, cationic, non-ionic, or zwitterionic. In some embodiments, anionic surfactants affected the stability of ferrate disinfectant solution less than ionic surfactants. In view thereof, anionic surfactants can be particularly suitable to include in a ferrate disinfectant solution. In some embodiments, surfactants having properties to function as wetting agents, emulsifiers, foaming agents, and/or dispersants can be included in the disinfectant solutions disclosed herein in addition to or alternatively to detergent surfactants.

In general, the concentration of any surfactant included in a ferrate disinfectant solution depends on the composition of other components in the solution as well as the intended function of the solution. In some cases, it is advantageous to have a relatively low concentration of a surfactant to lessen the rate of decomposition of the ferrate in the solution. A relatively low concentration of a detergent surfactant can also beneficial to limit the amount of bubbles in the solution. An exemplary concentration range for a surfactant in the ferrate disinfectant solutions disclosed herein is between about 0.5 g/L and about 2.0 g/L, but smaller or larger amounts are also included.

Another option for the disinfectant solutions disclosed herein is to include one or more fragrance compounds to provide a fragrance to disinfected surfaces.

As noted above, the disinfectant solutions disclosed herein include a solvent. In some embodiments, the solvent is water. In particular, the solvent can be distilled water, un-distilled water, tap water, potable water, non-potable water, and the like. In other cases, however, the solvent can be non-aqueous.

Regardless of the composition of the ferrate disinfectant solutions disclosed herein (i.e., regardless of the concentration of ferrate and the inclusion and concentration of a hypohalite salt, surfactant/s, and fragrance compounds), the pH of the disinfectant solutions can be between about 5.0 and about 13.0. Relatively weak caustic pH levels are advantageous because ferrate is less stable at acidic pH levels and strong caustic pH levels. Thus, in some embodiments, the pH of the disinfection solutions is between about 7.0 and about 12.0 and, in particular embodiments, the pH of the disinfection solutions is between about 8.0 and about 10.0 or between about 7.0 and about 9.0.

In general, the disinfectant solutions described herein are capable of disinfecting surfaces including about $1 \times 10^1$ microorganisms/cm$^2$ to about $1 \times 10^8$ microorganisms/cm$^2$ in less than approximately 30 seconds.

As used herein, the terms "about" and "approximately" refers to +/−5% of the recited value.

EXAMPLES

Example 1

Preparation of Liquid Ferrate Solution.

0.1% Bleach base solution was prepared by adding 2 ml of bleach (Walmart, 8.25%) in 200 ml of un-distilled water. To this solution, about 50 mg of solid material containing ferrate was added and dissolved immediately. This solution had characteristic color of ferrate and spectra had maxima at 510 nm wavelength (Rush and Bielski, 1986).

Test Organism Preparation.

0.5 McFarland solutions of MRSA and E. coli were prepared in un-distilled water using fresh growth of MRSA and E. coli on blood agar. The solution was serially diluted to achieve a target of 15 million organisms per milliliter to represent ($10^6$ solution) contamination.

Testing.

1 ml of liquid ferrate was mixed with 1 ml of test organism in a test tube for 1 to 5 minutes. It was then plated on blood agar plate and incubated for 24 hours at 37° C. The colony counts were read at 24 hours. This experiment was done for both MRSA and E. coli. Similarly, MRSA and E. coli were plated on blood agar plates without addition of liquid ferrate as controls and plates read after 24 hours of incubation.

Results.

The control organism plates grew confluent growth of MRSA and E. coli at 24 hours. The test plates that originally contained MRSA and E. coli demonstrated no growth at 24 hours. These experiments were repeated on 3 separate days. These experiments are summarized in Tables 1.

TABLE 1

| | MRSA & E. Coli | | | |
|---|---|---|---|---|
| Organism Type | Inoculum size | Contact time | Final Read Date | Colony Counts (Final Read) |
| MRSA | >1.5 million | 5 minutes | Nov. 30, 2016 | No growth |
| MRSA | >1.5 million | 5 minutes | Nov. 30, 2016 | No growth |
| MRSA | >1.5 million | 5 minutes | Nov. 30, 2016 | No growth |
| MRSA | >1.5 million | 5 minutes | Nov. 30, 2016 | No growth |
| MRSA | >1.5 million | NA | Nov. 30, 2016 | Confluent growth |
| MRSA | >1.5 million | 1 minute | Dec. 6, 2016 | No growth |
| MRSA | >1.5 million | 1 minute | Dec. 6, 2016 | No growth |
| MRSA | >1.5 million | 1 minute | Dec. 6, 2016 | No growth |
| MRSA | >1.5 million | 1 minute | Dec. 6, 2016 | No growth |
| Ecoli | >1.5 million | NA | Feb. 2, 2017 | Confluent growth |
| Ecoli | >1.5 million | 1 minute | Feb. 2, 2017 | No growth |
| MRSA | >1.5 million | 1 minute | Feb. 2, 2017 | No growth |
| MRSA | >1.5 million | NA | Feb. 2, 2017 | Confluent growth |

As shown in Tables 1, the ferrate solution was able to inhibit the growth of antibiotic-resistant pathogenic bacteria, such as MRSA and E. coli. The stability of this solution at room temperature with exposure to light and air was 24 hours. This is the first time a stable ferrate solution has been demonstrated to have antibacterial effect in disinfecting $10^6$ organisms on a surface.

Example 2

Preparation of Test Organisms:

The test organisms were prepared in sterile water using a microbial transfer loop. Vortexed×30 seconds and concentration initially titrated to 0.5 McFarland solution using a calibrated device. Then the 0.5 McFarland solution (3 mL) expected to contain $10^7$-$10^8$ organisms transferred to 30 mL of sterile water in a sterile container to achieve a target solution of $10^6$ organisms.

INITIAL Microbial Population:

The initial microbial preparation method is as described above. It was prepared in sterile water.

Initial MSSA: $1.5 \times 10^7$
Final MSSA: $1.0 \times 10^7$
Initial P. aeruginosa: $0.5 \times 10^7$
Final P. aeruginosa: $2.5 \times 10^6$ Process:

Test organisms (MSSA and P. aeruginosa) were mixed with liquid ferrate solutions at five concentrations (400 μM, 200 μM, 100 μM, 50 μM, 10 μM). The base was sterile water. The organism concentration was $10^7$, 0.5 mL. The test substrate was 9.5 mL. Mixing was done for two contact times: 1 minute and 2 minutes. Upon the contact time, measured by a calibrated watch, the organism and test substrate (1.0 mL) was transferred to 40 mL of D/E neutralizing broth for at least one hour. Then 0.1 mL of D/E neutral broth with organism and neutralized test solution plated to blood agar plates. Further, 0.1 mL was aliquoted to serial dilutions of $10^{-7}$. 0.1 ml of the liquid from the dilution tubes were then plated on to blood agar plates (Hardy diagnostics) and incubated at 35° C.±2° C. for 24 hours. Plates were enumerated and colony counts recorded as below. Only one plate was used for each concentration and time.

Results:

all plates were clean, no growth.

Neutralization:

All test substrates (10 μM, 50 μM, 100 μM, 200 μM, 400 μM) were added to 40 mL of Dey-Engley (D/E) neutralization broth. Let it sit for one hour after thoroughly vortexing it. Then 1 mL of MSSA stock solution ($10^6$ Concentration) and 1 mL of P. aeruginosa stock solution ($10^6$ concentration) were added to above mixture, vortex, aliquot to dilute and plated to blood agar plates and incubated and enumerated as above.

Example 3

Preparation of Test Organisms:

The test organisms were prepared in sterile water using the plate flooding method. Prior to flooding, C. diff toxigenic ATCC strain was cultured on above media under anaerobic conditions at 35° C. 2° C. for 14 days. Once incubated for this long it is assumed to have maximum >90% sporulation. Exposure of plates to aerobic conditions before flooding kills the germinated or alive C. diff leaving only spores. Methanol or Ethanol were not used to purify spores for fear of interference with testing as well as concern for altering mechanism of action of ferrate by altering pH. Direct stock solution of C. diff spores in sterile water was used to get maximum spore count as colorimetric method may yield <$10^6$ organisms/mL and is usually unreliable for spore counts.

Initial C. diff Population:

The initial C. diff population method is described above.

Initial C. diff population: $1.2 \times 10^6$
Final C. diff population: $0.5 \times 10^6$ Enumeration:

Test organism C. diff was mixed with three liquid ferrate solutions (400 μM, 200 μM, 100 μM). The liquid ferrate solutions were prepared in sterile water. The test organism was at $10^6$ concentration as described above. Mixed and tested for two contact times, 1 minute, and 2 minutes using a calibrated time device. After contact time the organism and test solution were transferred (1 mL) in 40 mL of D/E neutralizing broth and allowed to sit for at least one hour. Then 0.1 mL of D/E broth which has the test organism+ neutralized substrate was aliquoted and plated on C. diff media and serially diluted to $10^{-8}$. All plates were later incubated at 35° C.±2° C. for 48 hours and plate counts were read. Two plates were prepared for 2 contact times and 3 substrate concentrations.

Results:

All plates were clean, no growth, except plates with solutions containing 400 μM and tested at 1 minute exhibited growth in the $10^{-1}$-$10^{-2}$ dilutions. In addition, one plate coating with a solution containing 200 μM and tested at 2 minutes exhibited growth in $10^{-4}$ dilution.

Neutralization Test:

9.5 mL of the liquid ferrate solution (or substrate) at three concentrations (100 μM, 200 μM, 400 μM) of ferrate was added it to 40 mL of D/E broth. After sitting for an hour, 0.5 mL of C. diff was then added. Then 0.1 ml aliquot was removed and serially diluted to achieve a $10^{-8}$ concentration and plated them on C. diff media and incubated at 35° C.±2° C. for 48 hours. The broth was incubated directly in anaerobic conditions with all plates.

All plates with organisms, broth, were incubated in a 4.5-lt anaerobic jar with 3×1.5 L anaerobic condition producing pouches from Mitsubishi. A test indicator was placed in all 4 containers to assess anaerobic conditions.

Example 4

Preparation of Test Organisms:

The test organisms were prepared in sterile water using a microbial transfer loop. Vortexed×30 seconds and concentration initially titrated to 0.5 McFarland solution using a calibrated device. Then the 0.5 McFarland solution (3 mL) expected to contain $10^7$-$10^8$ organisms transferred to 30 mL of sterile water in a sterile container to achieve a target solution of $10^6$ organisms.

Initial Microbial Population:

The initial microbial preparation method is as described above. It was prepared in sterile water.

Initial MSSA: $1.0 \times 10^7$
Final MSSA: $5.5 \times 10^6$
Initial P. aeruginosa: $1.5 \times 10^6$
Final P. aeruginosa: $2 \times 10^5$ Process:

Test organisms (MSSA and P. aeruginosa (PA)) were mixed with three concentrations of ferrate (400 μm, 200 μm, 100 μm). The ferrate was stabilized. The base was sterile water. The organism was $10^7$ concentration, 0.5 mL. The test substrate was 9.5 mL. Mixed for two contact times: 1 minute. Upon the contact time measured by a calibrated watch the organism and test substrate (1.0 mL) was transferred to 40 mL of D/E neutralizing broth for at least one hour. Then 0.1 mL of D/E neutral broth with organism and neutralized test solution plated to blood agar plates. Further, 0.1 mL was aliquoted to serial dilutions of $10^{-7}$. 0.1 ml of the liquid from the dilution tubes were then plated on to blood agar plates (Hardy diagnostics) and incubated at 35°

C.±2° C. for 24 hours. Plates were enumerated and colony counts recorded as below. Only one plate was used for each concentration and time instead of two as recommended by ASTM.

Results:

MSSA: Fe 200 and 400 had no growth. Fe 100 had 1 colony at $10^{-7}$ indicating contamination. PA: Fe 200 and 400 had no growth. Fe 100 has 2 colonies at $10^{-3}$ indicating possible contamination.

Neutralization:

The test substrate (100 µm, 200 µm, 400 µm) was added it to 40 mL of D/E neutralization broth. The mixture was allowed to sit for one hour after thorough vortexing. Then 1 mL of MSSA stock solution and 1 mL of *P. aeruginosa* (PA) stock solution added to above mixture, vortexed, aliquoted to dilute and plated to blood agar plates and incubated and enumerated as above.

Example 5

Preparation of Test Organisms:

The test organisms were prepared in sterile water using the plate flooding method. Prior to flooding, *C. diff* toxigenic ATCC strain was cultured on above media under anaerobic conditions at 35° C.±2° C. for 14 days. Once incubated for this long it is assumed to have maximum >90% sporulation. Exposure of plates to aerobic conditions before flooding kills the germinated or alive *C. diff* leaving only spores. Methanol or Ethanol were not used to purify spores for fear of interference with testing as well as concern for altering MoA of ferrate by altering pH. We used direct stock solution of *C. diff* spores in SW to get maximum spore count as colorimetric method may yield <$10^6$ organisms/mL and is usually unreliable for spore counts.

Initial *C. diff* Population:

The initial *C. diff* population method is described above in SW.

Initial *C. diff* population: $2 \times 10^5$

Final *C. diff* population: Not performed as there is not much decline in spores.

Process:

Test organism *C. diff* was mixed with 3 ferrate concentrations (400 µM, 200 µM, 100 µM). The ferrate was prepared in sterile water. The test organism concentration was $10^6$ as described above (actual count $2 \times 10^5$). Mixed and tested for one contact time (1 minute) using a calibrated time device. After contact time the organism and test solution was transferred (1 mL) in 40 mL of D/E neutralizing broth and allowed to sit for at least one hour. Then 0.1 mL of D/E broth which has the test organism+neutralized substrate was aliquoted and plated on *C. diff* media and serially diluted to $10^{-7}$. All plates were later incubated at 35° C.±2° C. for 48 hours and plate counts were read. One plate was prepared for 1 contact times and 3 substrate concentrations.

Results:

All substrate samples tested negative for *C. diff* spore at 1 minute. All substrate concentration killed the $2 \times 10^5$ concentration of spores in 1 minute.

Neutralization:

9.5 mL of the three concentrations of test substrate (100 µM, 200 µM, 400 µM) ferrate were added it to 40 mL of D/E broth. We let it sit for an hour then added 0.5 mL of *C. diff*. Then 0.1 ml aliquots was removed and serially diluted to achieve a $10^{-7}$ concentration and plated them on *C. diff* media and incubated them at 35° C.±2° C. for 48 hours. The broth was directly incubated in anaerobic conditions with all plates.

All plates with organisms, broth, were incubated in a 4.5-lt anaerobic jar with 3×1.5 L anaerobic condition producing pouches from Mitsubishi. A test indicator was placed in all 4 containers to assess anaerobic conditions. D/E neutralization broth is an effective neutralizer.

Example 6

Preparation of Test Organisms:

Similar to previous rounds for MSSA, PA and C,

Initial Population:

The initial population method is as described before in SW.

Initial *C. diff* population: $3 \times 10^6$

Initial MSSA: $1 \times 10^7$

Initial PA: $1.5 \times 10^7$

Final *C. diff* population: Not done

Results:

There was no growth in the controls or substrate.

Enumeration:

Test organisms MSSA, PA and *C. diff* were mixed with 3 ferrate concentrations (400 µM, 200 µM, 100 µM) for 2 contact times of 1 minute and 30 seconds. The ferrate was prepared in sterile water. The test organism concentration was at least $10^6$ as described above. Mixed and tested for two contact times, 1 minute, and 30 seconds using a calibrated time device. After contact time the organism and test solution was transferred (1 mL) in 40 mL of D/E neutralizing broth and allowed to sit for at least one hour. Then 0.1 mL of D/E broth which has the test organism+neutralized substrate was aliquoted and plated on *C. diff* media and serially diluted to $10^{-7}$. All plates were later incubated at 35° C.±2° C. for 48 hours and plate counts were read. One plates were prepared for 2 contact times and 3 substrate concentrations and 3 organism types.

Results:

There was no growth in any of the organism+ferrate plates for any concentration and any of the contact times. Ferrate can achieve a 6 log reduction for MSSA, PA and *C. diff* in 30 seconds using Ferrate 100 µM, 200 µM, and 400 µM.

Neutralization:

9.5 mL of the three concentrations of test substrate (100 µM, 200 µM, 400 µM) ferrate were added it to 40 mL of D/E broth. It sat for an hour then added 0.5 mL of MSSA or PA or CDIFF. Then 0.1 ml aliquots were removed and serially diluted to achieve a $10^{-7}$ concentration and plated them on *C. diff* media and incubated them at 35° C.±2° C. for 48 hours. The broth was directly incubated in anaerobic conditions with all plates.

All plates with organisms, broth, were incubated in a 4.5-lt anaerobic jar with 3×1.5 L anaerobic condition producing pouches from Mitsubishi. A test indicator was placed in all 4 containers to assess anaerobic conditions.

Example 7

Figure 1A:
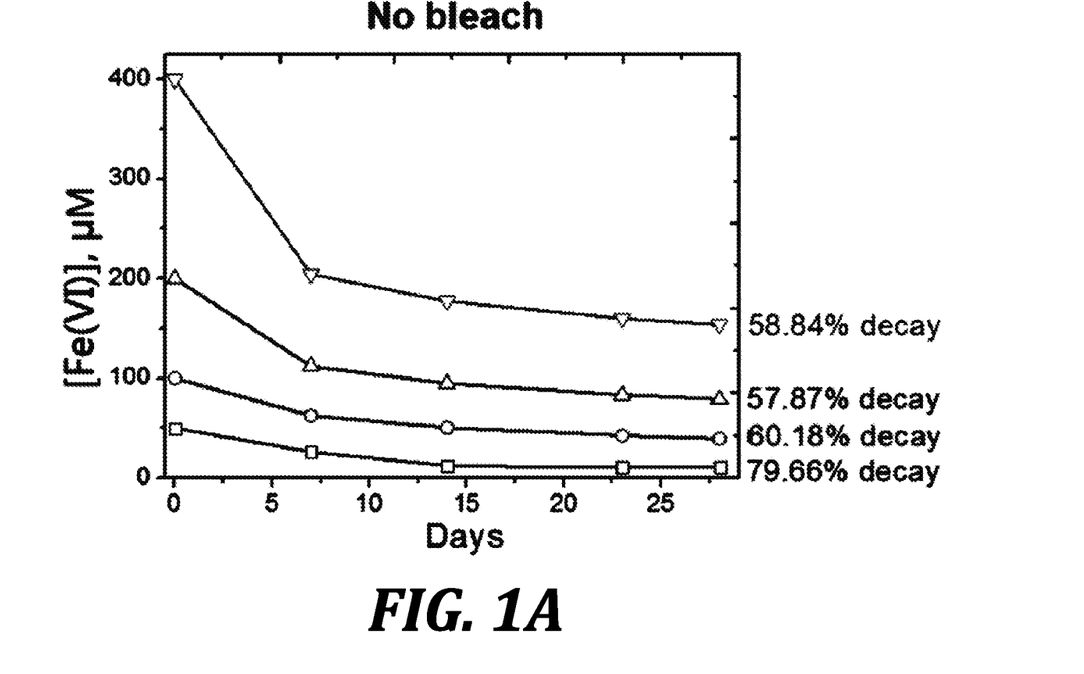
FIGS. 1A-1F show graphs of decay of disinfectant solutions having various initial concentrations of $Fe(VI)O_4^{2-}$ (50 μM, 100 μM, 200 μM, and 400 μM) with bleach concentrations of 0%, 0.02%, 0.05%, 0.1%, 0.5%, and 1.0% as a function of time, as indicated in each graph.
Figure 1B:
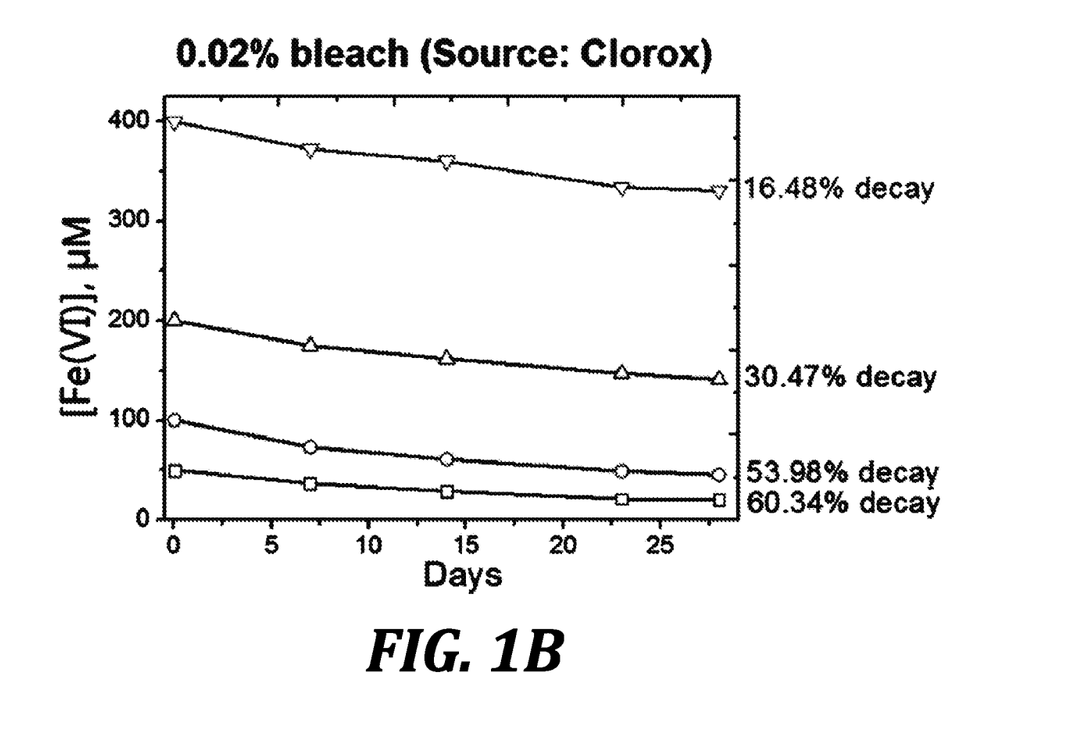
Figure 1C:
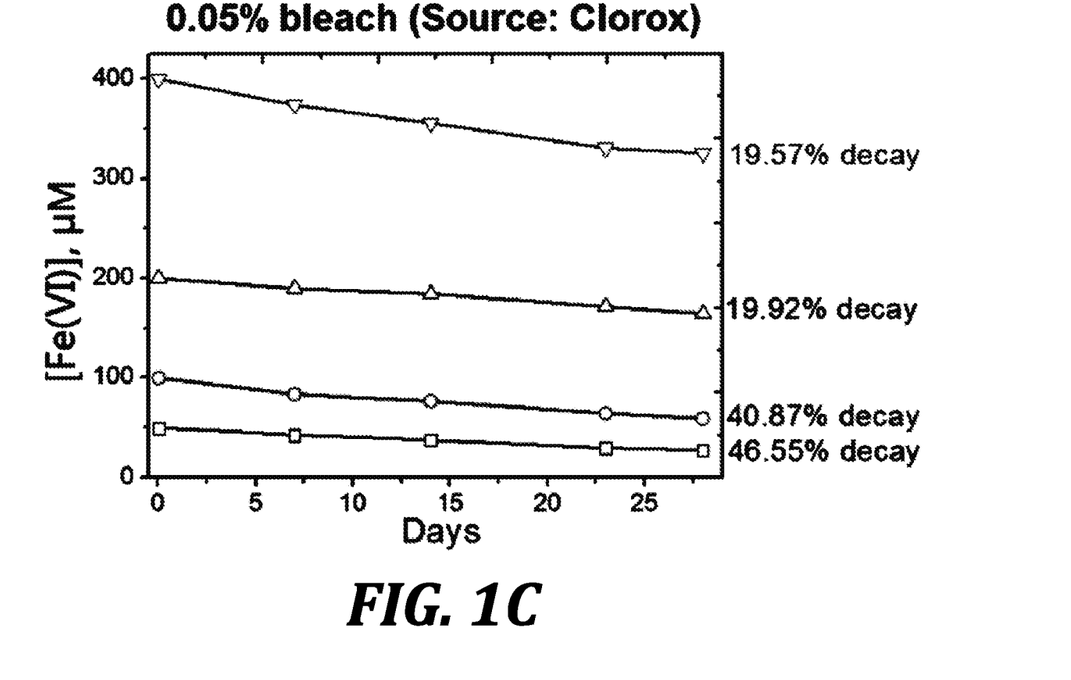
Figure 1D:
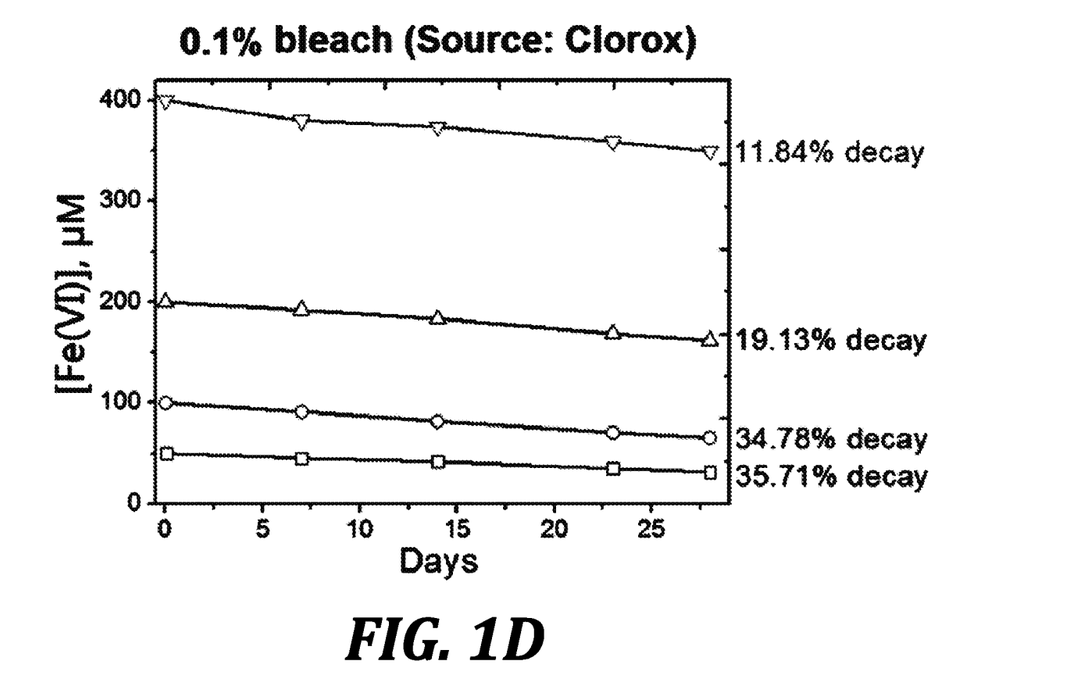
Figure 1E:
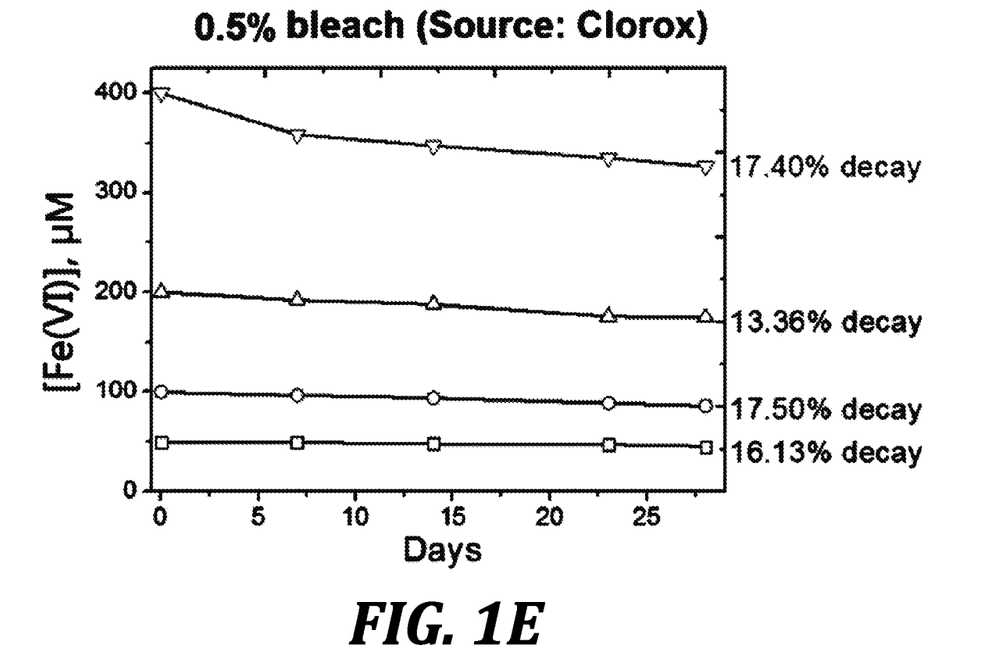
Figure 1F:
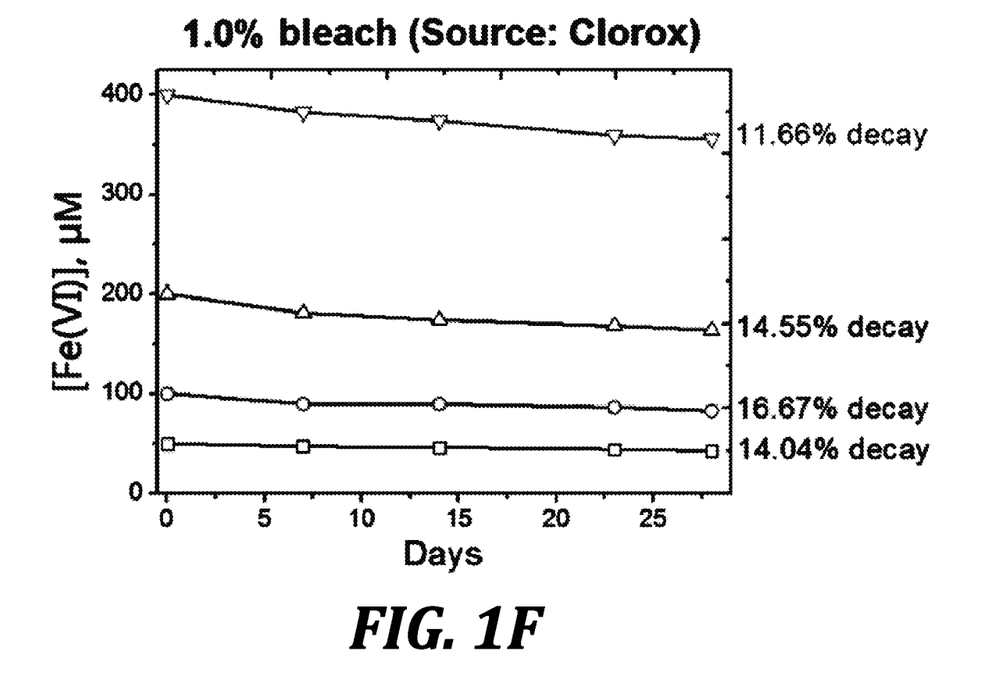

Initially, solutions of four concentrations of ferrate(VI) (Fe(VI), 50.0, 100.0, 200.0, and 400.0 µM) were prepared. Decrease in Fe(VI) concentration was monitored for 28 days. Concentrations of bleach were varied from 0.02% to 1.0%. Results are presented in FIG. 1. Increase in bleach percentage enhanced the stability of liquid Fe(VI). Percentage of decreasing Fe(VI) depends on both Fe(VI) and bleach concentrations. Fe(VI) could be stabilized for a long period of time in presence of bleach. With aim of having less of bleach due to practical applications, the amount of 0.1% appears reasonable. The decreased percentage of Fe(VI) was 35.7%, 34.8%, 19.1%, and 11.8% for 50.0, 100.0, 200.0, and 400.0 μM Fe(VI) after 28 days, respectively (FIG. 1*d*).

Example 8

Effect of four surfactants (sodium dodecyl sulfate (SDS), Tween 80, Tween 20, and Triton X-100) was evaluated. These surfactants are either anionic or non-ionic.

The stability of Fe(VI) was first tested at low levels of surfactant (1.0 and 10.0 mg/L) under two bleach concentrations (0.1% and 0.5%). In this set of stability experiments, the initial concentration of Fe(VI) was 200.0 μM. Fe(VI) was reasonably stable for 1 day under both bleach concentrations. There was less decrease in Fe(VI) concentration when 0.5% bleach was used. Comparatively, more stability of Fe(VI) was found in presence of SDS than three other surfactants.

In a third set of experiments, stability of Fe(VI) was tested at high concentrations of surfactants (0.5 and 1.0 g/L). Concentration of self-prepared bleach was 0.1%. Initial concentration of Fe(VI) was 200.0 μM. Concentration of Fe(VI) was measured for 7 days. Fe(VI) solution was highly unstable in presence of Tween 80, Tween 20, and Triton X-100, and the color of Fe(VI) solution almost completely disappeared after 1 day. Comparatively, Fe(VI) was relatively stable in SDS solution at both test concentrations. In presence of SDS and 0.1% bleach, decrease in Fe(VI) concentrations after 7 days was 50% and 70% at 0.5 and 1.0 g/L SDS solutions, respectively.

Finally, stability of Fe(VI) was tested at different concentrations of Fe(VI) (100.0, 200.0, and 400.0 μM), while bleach was from two sources, i.e., freshly prepared in lab and obtained from Walmart). Fe(VI) was in 0.1% bleach, and the concentrations of SDS were individually added as 0.5 and 1.0 g/L. Concentrations of Fe(VI) were determined after 5 days. Bleach obtained from Walmart showed highly unstable results of Fe(VI). Comparatively, Fe(VI) solution was much more stable in freshly prepared bleach in our laboratory. In this bleach solution, decrease in Fe(VI) was concentration-dependent of Fe(VI) and SDS. Concentration of Fe(VI) decreased from 400.0 to 250.0 μM in 5 days.

In summary, Fe(VI) was reasonably stable in SDS surfactant solution. This composition of Fe(VI) in mixed solution (0.1% bleach and SDS at 0.5 and 1.0 g/L) was thus tested as the disinfectant for bacterial inactivation.

While the preferred embodiment of the invention has been illustrated and described, it will be appreciated that various changes can be made therein without departing from the spirit and scope of the invention. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention.

The invention claimed is:

1. A liquid disinfectant solution, comprising:
    a ferrate having a concentration from approximately 50 to approximately 400 μM in the liquid disinfectant solution, wherein the ferrate comprises an oxycompound of iron in an oxidation state of six;
    a hypohalite salt having a concentration from approximately 0.02 to approximately 1.0 weight percent in the liquid disinfectant solution;
    sodium dodecyl sulfate (SDS) having a concentration from approximately 0.0010 to approximately 1.0 g/L in the liquid disinfectant solution; and
    water.

2. The liquid disinfectant solution of claim 1, wherein the ferrate has a concentration between approximately 100 μM and approximately 400 μM in the liquid disinfectant solution.

3. The liquid disinfectant solution of claim 1, wherein the hypohalite salt has a concentration between approximately 0.1 wt % and approximately 0.5 wt % in the disinfectant solution.

4. The liquid disinfectant solution of claim 1, wherein the hypohalite salt is sodium hypochlorite.

5. The liquid disinfectant solution of claim 1, wherein the liquid disinfectant solution has a pH between approximately 5.0 and approximately 13.0.

6. The liquid disinfectant solution of claim 1, wherein the liquid disinfectant solution has a pH between approximately 7.0 and approximately 12.0.

7. The liquid disinfectant solution of claim 1, wherein the liquid disinfectant solution has a pH between approximately 8.0 and approximately 10.0.

8. The liquid disinfectant solution of claim 1, wherein the ferrate material further comprises an alkali metal or an alkaline earth metal.

9. The liquid disinfectant solution of claim 1, wherein the water is tap water or distilled water.

10. The liquid disinfectant solution of claim 1, wherein the water is potable water or non-potable water.

* * * * *